United States Patent
Won et al.

(10) Patent No.: US 12,285,402 B2
(45) Date of Patent: Apr. 29, 2025

(54) COMPOSITIONS AND METHODS FOR TREATING PULMONARY DISORDERS

(71) Applicant: GNT Pharma Co., Ltd., Gyeonggi-do (KR)

(72) Inventors: Sojung Won, Hwaseong-si (KR); JinHwan Lee, Hwaseong-si (KR); Chun San Ahn, Yongin-si (KR); Sung Ig Cho, Seoul (KR); Byoung Joo Gwag, Yongin-Si (KR)

(73) Assignee: GNT PHARMA CO., LTD., Gyeonggi-do (KR)

( * ) Notice: Subject to any disclaimer, the term of this patent is extended or adjusted under 35 U.S.C. 154(b) by 0 days.

(21) Appl. No.: 18/089,920

(22) Filed: Dec. 28, 2022

(65) Prior Publication Data
US 2023/0233503 A1     Jul. 27, 2023

Related U.S. Application Data

(60) Provisional application No. 63/294,132, filed on Dec. 28, 2021.

(51) Int. Cl.
    *A61K 31/245*     (2006.01)
    *A61K 45/06*     (2006.01)
    *A61P 11/06*     (2006.01)

(52) U.S. Cl.
    CPC ............ *A61K 31/245* (2013.01); *A61K 45/06* (2013.01); *A61P 11/06* (2018.01)

(58) Field of Classification Search
    CPC .. A61K 31/167; A61K 31/196; A61K 31/245; A61K 31/606; A61P 11/06; A61P 11/00
See application file for complete search history.

(56) References Cited

U.S. PATENT DOCUMENTS 6,573,402 B1    6/2003    Gwag et al.
8,598,383 B2    12/2013    Gwag et al.
(Continued)

FOREIGN PATENT DOCUMENTS

WO    WO-2007119973 A1 *   10/2007   .......... A61K 31/136
WO    WO-2014/070859 A1    5/2014
(Continued)

OTHER PUBLICATIONS

Shukla et. al., Targeting Chronic Inflammatory Lung Diseases Using Advanced Drug Delivery Systems, Chapter 1, pp. 1-31, publ. 2020 (Year: 2020).*

(Continued)

*Primary Examiner* — Sarah Pihonak
(74) *Attorney, Agent, or Firm* — Harness, Dickey & Pierce, P.L.C.

(57) ABSTRACT

The present invention relates to pharmaceutical compositions and methods useful for treating pulmonary disorders, including asthma, chronic obstructive pulmonary disease (COPD), asthma-COPD overlap syndrome (ACOD), or any other respiratory diseases comprising 2-hydroxybenzoic acid derivatives of the formula (I) or a pharmaceutically acceptable salt thereof. Administration of a 2-hydroxybenzoic acid derivative of formula (I) significantly alleviates airway tissue damage and inflammation in animal models of asthma and COPD.

9 Claims, 8 Drawing Sheets

(56) References Cited

U.S. PATENT DOCUMENTS

| | | |
|---|---|---|
| 8,686,185 B2 | 4/2014 | Gwag et al. |
| 2020/0206172 A1 | 7/2020 | Lee et al. |
| 2023/0233503 A1 | 7/2023 | Won et al. |

FOREIGN PATENT DOCUMENTS

| | | |
|---|---|---|
| WO | WO-2021/181159 A1 | 9/2021 |
| WO | WO-2023/156808 A2 | 8/2023 |

OTHER PUBLICATIONS

International Search Report for Application No. PCT/IB/2022/000821 dated Sep. 19, 2023.

Lee et al., "Prevention effects of ND-07, a novel drug candidate with a potent antioxidative action and anti-inflammatory action, in animal models of severe acute pancreatitis", European Journal of Pharmacology, vol. 687, No. 1/3, pp. 28-38 (2012).

Vilvert et al., "Ex Vivo and In Vivo Evidence of Anti-Inflammatory Activity of P-aminophenol and Salicylate Derivatives", Current Bioactive Compounds, vol. 16, No. 5, pp. 593-605 (2020).

* cited by examiner

COMPOSITIONS AND METHODS FOR TREATING PULMONARY DISORDERS

RELATED APPLICATION

This application claims the benefit of priority to U.S. Provisional Patent Application Ser. No. 63/294,132, filed Dec. 28, 2021, which is hereby incorporated by reference in its entirety.

FIELD OF THE DISCLOSURE

The present invention relates to pharmaceutical compositions and methods to aid the treatment of asthma, chronic obstructive pulmonary disease (COPD), and asthma-COPD overlap syndrome (ACOD), comprising a 2-hydroxybenzoic acid derivative of formula (I) or its pharmaceutically acceptable salt.

BACKGROUND OF THE INVENTION

Asthma

Asthma is among the most common chronic conditions worldwide, affecting over 300 million individuals worldwide, with prevalence rates ranging from 1% to 16% in different countries in 2018 [*"The Global Asthma Report"* from www.globalasthmanetwork.org]. Although rarely fatal, the economic burden associated with asthma is heavy due to direct and indirect medical costs, including prescription drug costs, healthcare utilization, and productivity losses.

Asthma is characterized by chronic airway inflammation, bronchial hyper-responsiveness, reversible airway obstruction, and airway hyper-responsiveness to various stimuli. Airway inflammation is a hallmark of asthma and underscores many of the pathophysiological changes seen within asthmatic airways, resulting in the characteristic symptoms of asthma, such as wheezing, shortness of breath, chest tightness, and coughing.

Bronchodilators, such as $\beta_2$ agonists and anticholinergic agents, are prescribed to relieve symptoms by relaxing the muscles around the airways and helping clear mucus from the lungs. Leukotriene receptor antagonists prevent breathing problems, such as coughing, extra mucus in the chest and throat, and wheezing.

Airway inflammation in asthma patients can be controlled using inhaled corticosteroids (ICS). Patients with severe asthma are less responsive to ICS. Moreover, some asthma patients are resistant to ICS. The oral administration of corticosteroids can be used to treat severe asthma but causes side effects in most patients, which may result in poor adherence and quality of life.

Cysteinyl leukotrienes are pivotal inflammatory lipid mediators of bronchial asthma formed through the 5-lipoxygenase pathway of arachidonic acid, which increases during asthma exacerbations and plays a role in the pathogenesis of asthma by promoting bronchoconstriction, mucus secretion, tissue edema, and leukocyte infiltration. In support of this, 5-lipoxygenase inhibitors and cysteinyl leukotriene-receptor-1 antagonists (LTRAs) improve airflow function and reduce the frequency of asthma exacerbations.

Non-steroidal anti-inflammatory drugs (NSAIDs) possess potent anti-inflammatory activity through cyclooxygenase-2 (COX-2) inhibition. However, NSAIDs inhibit COX-1 and COX-2, causing severe side effects, such as gastrointestinal (GI) toxicity and myocardial infarction. Moreover, NSAIDs can induce bronchospasm and exacerbate asthma symptoms. Selective inhibition of the inducible $PGE_2$ downstream synthase microsomal prostaglandin E synthase (mPGES)-1 has emerged as a novel strategy to reduce side effects. Interestingly, LTRAs inhibit mPGES-1 activity and $PGE_2$ production without interfering with COX activities, suggesting that LTRAs may exert their anti-inflammatory effects by inhibiting the mPGES-1-mediated inflammatory pathway.

In asthma patients, oxidative stress is increased in the airways and systemic circulation and likely contributes to airway obstruction and inflammation, which may increase mucus secretion, smooth muscle contraction, and vascular permeability. Oxidative stress disrupts glucocorticoid receptor (GR) signaling, possibly leading to ICS insensitivity [1].

COPD

COPD is characterized by progressive airflow obstruction, which results largely from cigarette smoking and the inhalation of other pollutants. It caused 3.23 million deaths in 2019, resulting in substantial social and economic burdens worldwide [www who. int/news-room/fact-sheets/detail/the-top-10-causes-of-deathref].

Toxic particles of inhaled smoke and pollutants induce various pathophysiological events in COPD, including abnormal airway inflammation, airway wall tissue remodeling and thickening, gene reprogramming in airway epithelial cells, senescence and death of lung structural cells, and oxidative stress [2-4]. Such pathological events are accompanied by the symptoms of COPD, such as dyspnea difficulty, cough, mucus production, and wheezing. COPD has no cure, but its symptoms and complications are treatable. The types of current medications used for treating COPD and asthma still depend on the use of bronchodilators and corticosteroids. Bronchodilators alleviate dyspnea by reducing the resistive work and airway resistance. While corticosteroids reduce the inflammation in asthma patients to some extent, COPD patients respond poorly to them. Such insensitivity to corticosteroids is attributable to the inactivation of histone deacetylase 2, which represses glucocorticoid receptor activity.

Roflumilast, a phosphodiesterase-4 (PDE-4) inhibitor that reduces airway inflammation, has been approved for reducing the risk of COPD exacerbations. Over the past two decades, pharmacological research has been progressing toward finding new anti-inflammatory pharmacological approaches to treat COPD patients more adequately. Unfortunately, except for roflumilast, which inhibits the PDE-4 enzyme, many of these approaches to target specific cytokines or chemokines have failed to reach the clinical development stage or have failed in clinical trials [5]. In fact, in COPD, no dominant cytokine or chemokine is responsible for the disease. Therefore, a single target cannot be effective in all pathways. More research is needed to associate inflammatory endotypes to clinical outcomes and responses to more precise anti-inflammatory treatments currently in development [6]. Therefore, based on previous failures, effective and safe anti-inflammatory drugs are urgently needed to reduce the progression and exacerbations of COPD.

Oxidative stress is associated with corticosteroid resistance by suppressing glucocorticoid receptor activity and exacerbating COPD by impairing responses against pathogens and aggravating airway inflammation. Approaches targeting oxidative stress have beneficial effects in animal models of COPD and have been considered potential therapeutic candidates for treating COPD. While the beneficial effects of thiol-based antioxidants, such as N-acetylcysteine, remained controversial in 12 clinical trials conducted on COPD patients [7], COPD patients treated with N-acetylcysteine, erdostein, and carbocysteine exhibit decreased exacerbations and improved health status [8]. Antioxidant vitamins are positively and negatively associated with pulmonary function in COPD patients (Rahman, 2009). Notably, the target COPD patients sensitive to antioxidants have not been identified due to heterogeneity in study populations, dosing, and additional treatment.

SUMMARY OF THE INVENTION

2-Acetoxy-5-(2-4-(trifluoromethyl)-phenethylamino)-benzoic acid (ATPB) and its derivatives ATPB is a novel compound synthesized from lead structures based on sulfasalazine, which has antioxidant and anti-inflammatory activities [9], and aspirin, which has anti-inflammatory, antipyretic, and anti-pain activities [10, 11]. ATPB ["ND-07" as another code name; Chemical name:2-acetoxy-5-(2-4-(trifluoromethyl)-phenethylamino)-benzoic acid] exhibits a potent anti-inflammatory action through inhibition of mPGES-1, a terminal enzyme of prostaglandin-$E_2$ ($PGE_2$) biosynthesis and antioxidant action through hydroxyl radical scavenging [12].

ATPB effectively reduces airway tissue damage and inflammation in rodent models of asthma and COPD. The present invention relates to pharmacological compositions and methods for treating pulmonary diseases such as asthma, COPD, and ACOD.

The present invention provides ATPB or its derivatives as controllers for the treatment of pulmonary diseases such as asthma or COPD. The present invention also provides ATPB or its derivatives to complement steroid treatment or replace corticosteroid treatment during asthma or COPD exacerbations.

Accordingly, the first aspect of the invention comprises a composition for treating a pulmonary disease, wherein the composition comprises a pharmaceutically acceptable excipient and a therapeutically effective amount of a compound represented by the chemical formula 1 or a pharmaceutically acceptable salt thereof.

A second aspect of the invention comprises a method of treating a pulmonary disease in a subject afflicted therewith, comprising administering to the patient a therapeutically effective amount of a compound represented by the chemical formula 1 or a pharmaceutically acceptable salt thereof:

In some embodiments, chemical formula 1 is as described below.

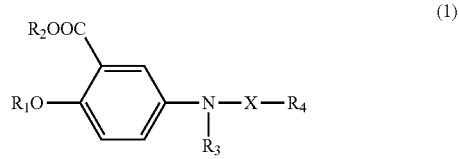

(1)

X is selected from CO, $SO_2$ and $(CH_2)_n$;

$R_1$ is selected from hydrogen, $C_1$-$C_6$ alkyl and $C_1$-$C_6$ alkanoyl;

$R_2$ is selected from hydrogen and $C_1$-$C_6$ alkyl;

$R_3$ is selected from hydrogen and a $C_1$-$C_5$ alkanoyl group; and $R_4$ is selected from phenyl, phenoxy, and 5- to 10-membered aryl groups, which is unsubstituted or substituted with one or more groups independently selected from nitro halogen, $C_1$-$C_6$ alkyl, $C_1$-$C_6$ haloalkyl, $C_1$-$C_5$ alkoxy, and $C_1$-$C_5$ haloalkoxy;

n is an integer from 1 to 5, inclusive;

or a pharmaceutically acceptable salt thereof.

In some embodiments the airway disorder is asthma, and the ATPB is used to treat asthma. In another embodiment, the airway disorder is COPD, and the ATPB is used to treat COPD.

In other embodiments, the airway disorder is an airway exacerbation, and the ATPB is used in treating or controlling airway exacerbation or disease.

Asthma and COPD are the most prevalent chronic respiratory diseases and have increased over recent decades. These two illnesses have many similarities and differences, which may sometimes hinder their diagnoses and management. Asthma-COPD ACOD occurs when patients have the characteristics of both asthma and COPD. The global prevalence of asthma, COPD, and ACOD are estimated to be 6.2%, 4.9%, and 2.0%, respectively [13].

Currently, no cure exists for asthma and COPD, and the only medications available for symptomatic management to some extent. Thus, new treatments with better efficacy and safety remain unmet medical needs for patients with asthma, COPD, and ACOD.

BRIEF DESCRIPTION OF THE FIGURES

The invention will be better understood by referring to the following description of several specific embodiments thereof, as shown in the accompanying figure.

DETAILED DESCRIPTION

Figure 1:
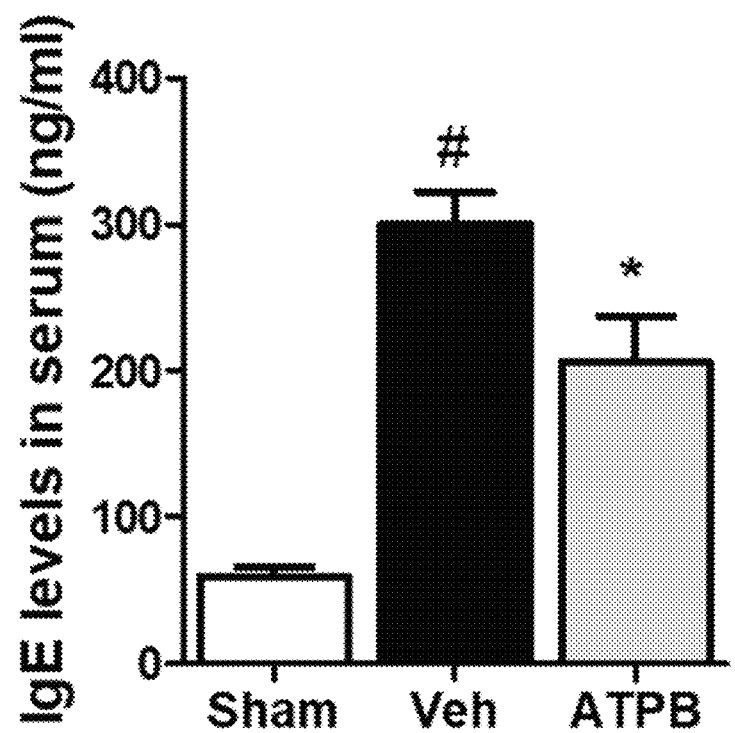
FIG. 1: Effects of ATPB on the Ovalbumin (OVA)-induced upregulation of serum immunoglobulin E (IgE) levels. Serum was collected 24 h after the last OVA aerosol challenge. The levels of OVA-specific IgE and total IgE were analyzed by enzyme-linked immunosorbent assay (ELISA). ATPB significantly lowered OVA-specific IgE levels, indicating OVA-specific inhibition of the Th2 response.

Airway disorders such as COPD and asthma involve multiple inflammatory cells and various mediators. ATPB effectively reduces smoking-induced inflammatory cell recruitment into the BALF, as well as TNF-α levels, IL-6 levels and MCP-1 gene expression in pulmonary tissues, pulmonary eosinophilia, and mucus hypersecretion in rat COPD models. ATPB attenuated OVA-induced inflammatory cell recruitment into the BALF, IL-4, IL-5, eotaxin production, serum IgE synthesis, pulmonary eosinophilia, and mucus hypersecretion in a mouse asthma model. Our findings support the novel therapeutic use of ATPB to treat airway disorders.

The present invention provides ATPB as a controller for treating airway disorders such as asthma or COPD. The present study provides ATPB to complement or replace steroid treatment during asthma or COPD exacerbations.

Compositions and Methods of the Invention

To achieve this objective, the present invention provides compositions for treating at least one pulmonary disease selected from asthma, COPD, and/or ACOD in a patient afflicted therewith, wherein the composition comprises a pharmaceutically acceptable excipient and a therapeutically effective amount of a compound represented by chemical formula 1 or its pharmaceutically acceptable salt thereof:

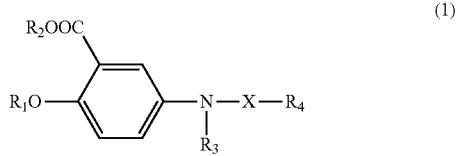

(1)

wherein,
X is selected from CO, $SO_2$ and $(CH_2)_n$;
$R_1$ is selected from hydrogen, $C_1$-$C_6$ alkyl and $C_1$-$C_6$ alkanoyl;
$R_2$ is selected from hydrogen and $C_1$-$C_6$ alkyl;
$R_3$ is selected from hydrogen and a $C_1$-$C_5$ alkanoyl group;
$R_4$ was selected from a phenoxy group and 5- to 10-membered aryl groups,
which is unsubstituted or substituted with one or more groups independently selected from nitro, halogen, $C_1$-$C_6$ alkyl, $C_1$-$C_6$ haloalkyl, $C_1$-$C_5$ alkoxy, and $C_1$-$C_5$ haloalkoxy; and
n is an integer from 1 to 5.

In certain embodiments,
X is $(CH_2)_n$;
$R_1$ is $C_1$-$C_6$ alkanoyl;
$R_2$ is hydrogen;
$R_3$ is hydrogen;
$R_4$ is a 5- to 10-membered aryl group that is unsubstituted or substituted with one or more groups independently selected from nitro, halogen, $C_1$-$C_6$ alkyl, $C_1$-$C_6$ haloalkyl, $C_1$-$C_5$ alkoxy, and $C_1$-$C_5$ haloalkoxy; and
n is an integer from 1 to 5, inclusive.

In certain embodiments, the 5- to 10-membered aryl group is a phenyl group. In certain embodiments, the phenyl is substituted. In other embodiments, the phenyl is unsubstituted.

In certain embodiments, n is 2.

In certain embodiments, $R_2$ is hydrogen.

In certain embodiments, $R_1$ is hydrogen or —C(O)alkyl. In other embodiments, $R_1$ is hydrogen. In other embodiments, $R_1$ is —C(O)alkyl. In other embodiments, $R_1$ is —C(O)CH$_3$. Several compounds of this formula (I) have been prepared and evaluated. In certain embodiments, the composition and methods comprise a 5-benzylaminosalicylic acid compound of formula (I) or its pharmaceutically acceptable salt.

In certain embodiments, the 5-benzylaminosalicylic acid compound is 5-benzylaminosalicylic acid.

Preferable examples of 5-benzylaminosalicylic acid compounds include, but are not limited to, 2-hydroxy-5-phenethylamino-benzoic acid (Compound 1), 2-hydroxy-5-[2-(4-trifluoromethyl-phenyl)-ethylamino]-benzoic acid (Compound 2), 2-hydroxy-5-[2-(3-trifluoromethyl-phenyl)-ethylamino]-benzoic acid (Compound 3), 5-[2-(3,5-bistrifluoromethyl-phenyl)-ethylamino]-2-hydroxy-benzoic acid (Compound 4), 2-hydroxy-5-[2-(2-nitro-phenyl)-ethylamino]-benzoic acid (Compound 5), 5-[2-(4-chloro-phenyl)-ethylamino]-2-hydroxy-benzoic acid (Compound 6), 5-[2-(3,4-difluoro-phenyl)-ethylamino]-2-hydroxy-benzoic acid (Compound 7), 5-[2-(3,4-dichloro-phenyl)-ethylamino]-2-hydroxy-benzoic acid (Compound 8), 5-[2-(4-fluoro-2-trifluoromethylphenyl)-ethylamino]-2-hydroxy-benzoic acid (Compound 9), 5-[2-(2-fluoro-4-trifluoromethyl-phenyl)-ethylamino]-2-hydroxy-benzoic acid (Compound 10), 2-hydroxy-5-[2-(4-methoxy-phenyl)-ethylamino]-benzoic acid (Compound 11), 2-hydroxy-5-(2-o-tolylethylamino)-benzoic acid (Compound 12), 2-hydroxy-5-(3-phenyl-propylamino)-benzoic acid (Compound 13), 2-hydroxy-5-[3-(4-trifluoromethyl-phenyl)-propylamino]-benzoic acid (Compound 14), 5-[3-(4-fluoro-phenyl)-propylamino]-2-hydroxy-benzoic acid (Compound 15), 5-[3-(3,4-dichloro-phenyl)-propylamino]-2-hydroxy-benzoic acid (Compound 16), 2-hydroxy-5-(3-p-tolyl-propylamino)-benzoic acid (Compound 17), 2-acetoxy-5-[2-(4-trifluoromethyl-phenyl)-ethylamino]-benzoic acid (Compound 18), 5-[2-(2-chloro-phenyl)-ethylamino]-2-hydroxy-benzoic acid (Compound 19), 5-benzylaminosalicylic acid (Compound 20), 5-(4-nitrobenzyl)aminosalicylic acid (Compound 21), 5-(4-chlorobenzyl)aminosalicylic acid (Compound 22), 5-(4-trifluoromethylbenzyl)aminosalicylic acid (Compound 23), 5-(4-fluorobenzyl)aminosalicylic acid (Compound 24), 5-(4-methoxybenzyl)aminosalicylic acid (Compound 25), 5-(2,3,4,5,6-pentafluorobenzyl)aminosalicylic acid (Compound 26), 5-(4-nitrobenzyl)amino-2-hydroxy ethylbenzoate (Compound 27), 5-(4-nitrobenzyl)-Nacetylamino-2-hydroxy ethylbenzoate (Compound 28), 5-(4-nitrobenzyl)-N-acetylamino-2-acetoxy ethylbenzoate (Compound 29), 5-(4-nitrobenzoyl)aminosalicylic acid (Compound 30), 5-(4-nitrobenzenesulfonyl)aminosalicylic acid (Compound 31), 5-[2-(4-nitrophenyl)-ethyl]aminosalicylic acid (Compound 32), and 5-[3-(4-nitro-phenyl)-npropyl]aminosalicylic acid (Compound 33).

In certain preferred embodiments, the compound of formula (I) is compound 18, 2-acetoxy-5-[2-(4-trifluoromethyl-phenyl)-ethylamino]-benzoic acid, or a pharmaceutically acceptable salt thereof, as a therapeutic agent for treatingasthma, COPD, and ACOD. In some embodiments, the compound with formula (I) has the structure 2-acetoxy-5-[2-(4-trifluoromethyl-phenyl)-ethylamino]-benzoic acid (Compound 18):

(18)

In certain preferred embodiments, the compound of formula (I) is 2,2-hydroxy-5-[2-(4-trifluoromethylphenyl) ethylamino]benzoic acid (Compound 2) or a pharmaceutically acceptable salt thereof. In some embodiments, the compound of formula (I) has the following structure:

In certain embodiments, the compound of formula (I) is selected from 2-acetoxy-5-[2-(4-trifluoromethyl-phenyl)-ethylamino-benzoic acid (compound 18; ATPB) and 2-hydroxy-5-2-(4-trifluoromethyl-phenyl)-ethylamino-benzoic acid (compound 2), and the at least one pulmonary disease is selected from asthma, COPD, and ACOD.

In certain embodiments, the compound of formula (I) is 2-acetoxy-5-[2-(4-trifluoromethyl-phenyl)-ethylamino-benzoic acid (ATPB), and the at least one pulmonary disease is selected from asthma, COPD, and AOCD.

In certain embodiments, the compound of formula (I) is a pharmaceutically acceptable salt.

In certain embodiments, the composition is in the form of a powder.

In certain embodiments, the composition is suitable for oral administration.

In certain embodiments, the composition is a pharmaceutical composition.

The present invention also provides a method of treating at least one pulmonary disease selected from asthma, COPD, ACOD, pulmonary fibrosis, pneumonia, and lung cancer, in a subject afflicted therewith, comprising administering to the patient having the at least one pulmonary disease a therapeutically effective amount of a compound represented by the chemical formula 1 or a pharmaceutically acceptable salt thereof:

(1)

wherein, X is selected from CO, $SO_2$ and $(CH_2)_n$;
$R_1$ is selected from hydrogen, $C_1$-$C_6$ alkyl and $C_1$-$C_6$ alkanoyl;
$R_2$ is selected from hydrogen and $C_1$-$C_6$ alkyl;
$R_3$ is selected from hydrogen and a $C_1$-$C_5$ alkanoyl group;
$R_4$ is selected from a phenoxy group and a 5- to 10-membered aryl group that is unsubstituted or substituted with one or more groups independently selected from nitro, halogen, $C_1$-$C_6$ alkyl, $C_1$-$C_6$ haloalkyl, $C_1$-$C_5$ alkoxy, and $C_1$-$C_5$ haloalkoxy; and
n is an integer from 1 to 5, inclusive.

In certain embodiments, wherein
X is $(CH_2)_n$;
$R_1$ is $C_1$-$C_6$ alkanoyl;
$R_2$ is hydrogen;
$R_3$ is hydrogen; and
$R_4$ is a 5- to 10-membered aryl group that is unsubstituted or substituted with one or more groups independently selected from nitro, halogen, $C_1$-$C_6$ alkyl, $C_1$-$C_6$ haloalkyl, $C_1$-$C_5$ alkoxy, and $C_1$-$C_5$ haloalkoxy; and
n is an integer from 1 to 5, inclusive.

In certain embodiments, the 5- to 10-membered aryl group is a phenyl group. In certain embodiments, the phenyl is substituted. In other embodiments, the phenyl is unsubstituted.

In certain embodiments, n is 2.
In certain embodiments, $R_2$ is hydrogen.
In certain embodiments, $R_1$ is hydrogen or —C(O)alkyl. In other embodiments, $R_1$ is hydrogen. In other embodiments, $R_1$ is —C(O)alkyl. In other embodiments, $R_1$ is —C(O)CH_3.

Several compounds of this formula (I) have been prepared and evaluated. In certain embodiments, the composition and methods comprise a 5-benzylaminosalicylic acid compound of formula (I) or its pharmaceutically acceptable salt.

In certain embodiments, the compound of formula (I) is selected from the group consisting of 2-hydroxy-5-phenethylamino-benzoic acid, 2-hydroxy-5-[2-(4-trifluoromethyl-phenyl)-ethylamino]-benzoic acid, 2-hydroxy-5-[2-(3-trifluoromethylphenyl)-ethylamino]-benzoic acid, 5-[2-(3,5-bis-trifluoromethyl-phenyl)-ethylamino]-2-hydroxy-benzoic acid, 2-hydroxy-5-[2-(2-nitro-phenyl)-ethylamino]-benzoic acid, 5-[2-(4-chloro-phenyl)-ethylamino]-2-hydroxy-benzoic acid, 5-[2-(3,4-difluoro-phenyl)-ethylamino]-2-hydroxy-benzoic acid, 5-[2-(3,4-dichloro-phenyl)-ethylamino]-2-hydroxy-benzoic acid, 5-[2-(4-fluoro-2-trifluoromethyl-phenyl)-ethylamino]-2-hydroxybenzoic acid, 5-[2-(2-fluoro trifluoromethyl-phenyl)-ethylamino]-2-hydroxy-benzoic acid, 2-hydroxy-5-[2-(4-methoxy-phenye-ethylamino]-benzoic acid, 2-hydroxy-5-(2-o-tolyl-ethylamino)-benzoic acid, 2-hydroxy-5-(3-phenyl-propylamino)-benzoic acid, 2-hydroxy-5-[3(4-trifluoromethyl-phenyl)-propylamino]-benzoic acid, 5-[3-(4-fluorophenyl)-propylamino]-2-hydroxy-benzoic acid, 5-[3-(3,4-dichloro-phenyl)-propylamino]-2-hydroxybenzoic acid, 2-hydroxy-5-(3-p-tolyl-propylamino)-benzoic acid, 2-acetoxy-5-[2-(4-trifluoromethyl-phenyl)-ethylamino]-benzoic acid, 5-[2-(2-chloro-phenyl)-ethylamino]-2-hydroxy-benzoic acid, 5-benzylaminosalicylic acid, 5-(4-nitrobenzyl)aminosalicylic acid, 5-(4-chlorobenzyl)aminosalicylic acid, 5-(4-trifluoromethylbenzyl)aminosalicylic acid, 5-(4-fluorobenzyl)aminosalicylic acid, 5-(4-methoxybenzyl)aminosalicylic acid, 5-(2,3,4,5,6-pentafluorobenzyl)aminosalicylic acid, 5-(4-nitrobenzyl)amino-2-hydroxy ethylbenzoate, 5-(4-nitrobenzyl)-N-acetylamino-2-hydroxy ethylbenzoate, 5-(4-nitrobenzyl)-N-acetylamino-2-acetoxy ethylbenzoate, 5-(4-nitrobenzoyl)aminosalicylic acid, 5-(4-nitrobenzenesulfonyl)aminosalicylic acid, 5-[2-(4-nitrophenyl)-ethyl]aminosalicylic acid, and 5-[3-(4-nitrophenyl)-npropyl]aminosalicylic acid. In certain embodiments, wherein the compound of formula (I) is selected from 2-acetoxy-5-[2-(4-trifluoromethyl-phenyl)-ethylamino-benzoic acid (compound 18; ATPB) and 2-hydroxy-5-2-(4-trifluoromethyl-phenyl)-ethylamino-benzoic acid (compound 2), and the at least one pulmonary disease is selected from asthma, COPD, and ACOD.

In certain embodiments, wherein the compound of formula (I) is 2-acetoxy-5-2-(4-trifluoromethyl-phenyl)-ethylamino-benzoic acid (ATPB), and at least one pulmonary disease is selected from asthma, COPD, and AOCD.

In certain embodiments, the compound of formula (I) is a pharmaceutically acceptable salt.

In certain embodiments of the method, the compound is present in a composition also comprising a pharmaceutically acceptable excipient.

In certain embodiments, the composition is in the form of a powder.

In certain embodiments, the composition is administered orally.

In certain embodiments, the at least one pulmonary disease is asthma.

In certain embodiments, the asthma is selected from glucocorticoid-resistant asthma and pediatric asthma.

In certain embodiments, the composition for treating asthma, in combination with one or more additional therapeutic agents for treating asthma to the patient.

In certain embodiments, the method further comprising conjointly or concurrently administering one or more additional therapeutic agents for treating asthma to the patient.

In certain embodiments, the one or more additional therapeutic agents for treating asthma are selected from corticosteroids (e.g., hydrocortisone, budesonide, methylprednisolone, fluticasone, mometasone, and dexamethasone).

In certain embodiments, the one or more additional therapeutic agents for treating asthma are selected from $\beta_2$ agonists (e.g., short-acting or long-acting bronchodilators, such as formoterol and salmeterol).

In certain embodiments, one or more additional therapeutic agents for treating asthma are selected from anticholinergics (e.g., ipratropium, oxitropium, and tiotropium).

In certain embodiments, the one or more additional therapeutic agents for treating asthma are selected from leukotriene receptor antagonists (e.g., montelukast, zafirlukast) or 5-lipoxygenase inhibitors (e.g., zileuton).

In certain embodiments, the one or more additional therapeutic agents for treating asthma are selected from oral xanthines (e.g., theophylline and aminophylline).

In certain embodiments, the one or more additional therapeutic agents for treating asthma are selected from antihistamines (e.g., levocetirizine, fexofenadine).

In certain embodiments, the one or more additional therapeutic agents for treating asthma are selected from anti-IgE antibody therapies (e.g., omalizumab).

In certain embodiments, the one or more additional therapeutic agents for treating asthma are selected from anti-interleukin-5 therapies (e.g., benralizumab, mepolizumab, reslizumab).

In certain embodiments, the one or more additional therapeutic agents for treating asthma are selected from corticosteroids, $\beta_2$ agonists, anticholinergics, leukotriene receptor antagonists, 5-lipoxygenase inhibitors, oral xanthines, antihistamines, anti-IgE antibody therapies, and anti-interleukin-5 therapies.

In certain embodiments, the at least one pulmonary disease is COPD and ACOD.

In certain embodiments, the composition for treating COPD or ACOD, in combination with one or more additional therapeutic agents for COPD or ACOD in the patient.

In certain embodiments, the method further comprising conjointly or concurrently administering one or more additional therapeutic agents for treating COPD or ACOD in the patient.

In certain embodiments, the one or more additional therapeutic agents for treating COPD or ACOD are selected from corticosteroids (e.g., beclomethasone, ciclesonide, budesonide, fluticasone).

In certain embodiments, the one or more additional therapeutic agents for treating COPD or ACOD are selected from $\beta_2$ agonists with short-acting or long-acting bronchodilation (e.g., fenoterol, salbutamol, formoterol, salmeterol, and indacaterol).

In certain embodiments, the one or more additional therapeutic agents for treating COPD or ACOD are selected from anticholinergics (e.g., ipratropium).

In certain embodiments, the one or more additional therapeutic agents for treating COPD or ACOD are selected from the long-acting muscarinic receptor antagonists (LAMAs) (e.g., tiotropium bromide, glycopyrronium bromide, and aclidinium bromide).

In certain embodiments, the one or more additional therapeutic agents for treating COPD or ACOD are selected from phosphodiesterase 4 (PDE4) inhibitors (e.g., roflumilast).

In certain embodiments, the one or more additional therapeutic agents for treating COPD or ACOD are selected from corticosteroids, β2 agonists with short-acting or long-acting bronchodilation, anticholinergics, LAMAs, and PDE4 inhibitors (e.g., fluticasone/salmeterol, budesonide/formoterol, and Ipratropium/β2 agonists).

In certain embodiments, the composition for treating wherein the treating comprises reducing any pathologically increased TH2 cytokines (e.g., TNF-α, IL-6, and/or MCP-1) in the patient.

In certain embodiments, the method wherein the treating comprises reducing any pathologically increased TH2 cytokines (e.g., TNF-α, IL-6, and/or MCP-1) in the patient.

In certain embodiments, the composition for treating wherein the treating comprises reducing any pathologically increased TH2 cytokines (e.g., IL-4 and/or IL-5) in the patient.

In certain embodiments, the method wherein the treating comprises reducing any pathologically increased TH2 cytokines (e.g., IL-4 and/or IL-5) in the patient.

In certain embodiments, the composition for treating wherein the dosage of the compound for treating the patient is approximately 1 µg/kg to approximately 200 mg/kg per day.

In certain embodiments, the method wherein a dosage of about 1 µg/kg to about 200 mg/kg per day of the compound is administered to the patient.

The 5-benzylaminosalicylic acid compound or its pharmaceutically acceptable salt of the present disclosure can be prepared by, but not limited to, the reaction schemes represented in U.S. Pat. No. 6,573,402, which is herein incorporated by reference.

2-acetoxy-5-2-(4-trifluoromethyl-phenyl)-ethylamino-benzoic acid (Compound 18), the preferable example of the present invention, can be prepared by but is not limited to the reaction schemes represented in U.S. Pat. Nos. 8,598,383 and 8,686,185, each of which are herein incorporated by reference.

2-hydroxy-5-2-(4-trifluoromethyl-phenyl)-ethylamino-benzoic acid (Compound 2), a preferable example of the present invention, can be prepared by, but is not limited to, the reaction schemes represented in U.S. Pat. No. 8,598,383, which is herein incorporated by reference.

Next, pharmaceutical compositions for treating or preventing COPD and asthma and the methods for treating or preventing COPD and asthma are described in greater detail.

Definitions

The definitions of the terms described below apply to the use of the terms independently or in combination with other terms.

The term "acetoxy" refers to a group represented by the general formula hydrocarbylC(O)O—, preferably alkylC(O)O—.

The term "acetyl" refers to a group represented by the general formula, CH$_3$ C(O). An "alkyl" group (including 'alkyl' of haloalkyl) or "alkane" is a straight-chained or branched non-aromatic hydrocarbon that is completely saturated. Typically, a straight chained or branched alkyl group has 1 to approximately 20 carbon atoms, preferably from 1 to approximately 10 unless otherwise defined. A C$_1$-C$_6$ straight-chained or branched alkyl group is called a "lower alkyl" group. In some embodiments, the alkyl is C$_1$-C$_5$ alkyl, preferably C$_1$-C$_3$ alkyl. More specifically, preferable alkyl groups include, but are not limited to, methyl, ethyl, propyl, isopropyl, butyl, sec-butyl, and tert-butyl.

Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. If not otherwise specified, such substituents can include, for example, a halogen, a hydroxyl, a carbonyl (such as a carboxyl, an alkoxy carbonyl, a formyl, or an acyl such as an alkylC(O), a thiocarbonyl (such as a thioester, thioacetate, or thioformate), alkoxyl, phosphoryl, phosphate, phosphonate, phosphinate, amino, amido, amidine, imine, cyano, nitro, azido, silyl ether, sulfhydryl, alkylthio, sulfate, sulfonate, sulfamoyl, sulfonamido, sulfonyl, heterocyclyl, aralkyl, or aromatic or heteroaromatic moieties. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl, and sulfonate), and silyl groups, as well as ethers, alkylthiols, carbonyls (including ketones, aldehydes, carboxylates, and esters), —CF$_3$, and —CN. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "Cx-y," when used in conjunction with a chemical moiety, such as acyl, acyloxy, alkyl, alkenyl, alkynyl, or alkoxy, indicates the inclusion of groups that contain from x to y carbons in the chain. For example, "Cx-y alkyl" refers to substituted or unsubstituted saturated hydrocarbon groups, including straight-chain alkyl and branched chain alkyl groups that contain from x to y carbons in the chain, including haloalkyl groups such as trifluoromethyl and 2,2,2-tirfluoroethyl, etc. C$_0$ alkyl indicates a hydrogen where the group is in a terminal position, a bond if internal. The terms "C2-alkenyl" and "C2-alkynyl" refer to substituted or unsubstituted unsaturated aliphatic groups analogous in length and possible substitution to the alkyls described above, but that contain at least one double or triple bond, respectively.

The term "alkanoyl" refers to a group represented by the general formula hydrocarbyl-C(O), preferably alkyl-C(O)—.

The term "alkoxy" (including 'alkoxy' of haloalkoxy) refers to an alkyl group, preferably a lower alkyl group, having an oxygen attached thereto. In some embodiments, preferably, the alkoxy is C1-C5 alkoxy, and more preferably C1-C3 alkoxy. More specifically, preferable alkoxy includes, but is not limited to, methoxy, ethoxy, and propanoxy. Halogen includes, but is not limited to, fluoride, chloride, bromide, and iodide. Preferably, alkanoyl is C$_2$-C$_{10}$ alkanoyl, and more preferably C3-C5 alkanoyl. More specifically, preferable alkanoyl includes, but is not limited to, ethanoyl, propanoyl, and cyclohexanecarbonyl.

The terms "amine" and "amino" are art-recognized and refer to both unsubstituted and substituted amines and salts thereof, e.g., a moiety that can be represented by,

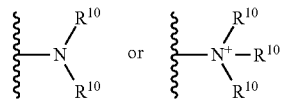

wherein each R$^{10}$ independently represents a hydrogen or a hydrocarbyl group, or two R$^{10}$ are taken together with the N atom to which they are attached complete a heterocycle having from 4 to 8 atoms in the ring structure.

The term "aryl," as used herein, include substituted or unsubstituted single-ring aromatic groups in which each atom of the ring is carbon. Preferably the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

The terms "halo" and "halogen," as used herein, mean halogens and includes chloro, fluoro, bromo, and iodo.

The term "lower," when used in conjunction with a chemical moiety, such as acyl, acyloxy, alkyl, alkenyl, alkynyl, or alkoxy, is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain preferred embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties containing substituents replacing a hydrogen atom on one or more carbon atoms of the backbone. that the terms "substitution" and "substituted with" implicitly include the proviso that such substitution is in accordance with a permitted valence of the substituted atom and the substituent and that the substitution results in a stable compound, e.g., which does not spontaneously transform by means such as rearrangement, cyclization or elimination, etc. As used herein, "substituted" includes all permissible substituents in organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for the appropriate organic compounds. For this invention, heteroatoms such as nitrogen may have hydrogen substituents and/or any permissible substituents of the organic compounds described herein that satisfy the valences of the heteroatoms. Substituents can include any substituents described herein, for example, a halogen, haloalkyl, hydroxyl, carbonyl (such as carboxyl, alkoxycarbonyl, formyl, or acyl), thiocarbonyl (such as thioester, thioacetate, or thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, aryl, or aromatic or heteroaromatic moiety. It will be understood by those skilled in the art that substituents can themselves be substituted, if appropriate. Unless specifically stated as "unsubstituted," references to chemical moieties herein include substituted variants. For example, reference to an "aryl" group or moiety implicitly includes substituted and unsubstituted variants.

The phrase "conjoint administration," as used herein, refers to any form of administration of two or more different therapeutic agents such that the second agent is administered while the previously administered therapeutic agent is still effective in the body (e.g., the two agents are simultaneously effective in the patient, which may include synergistic effects of the two agents). For example, different therapeutic compounds can be administered either concomitantly or sequentially in the same formulation or separate formulations. Thus, an individual receiving such treatment can benefit from the combined effects of different therapeutic agents.

The term "pharmaceutically acceptable salt," as used in the present disclosure refers to salts produced by non-toxic or slightly toxic acids or bases. Pharmaceutically acceptable base addition salt includes, but is not limited to, sodium, potassium, calcium, ammonium, magnesium or salt made by organic amino. In case that the compound of the present disclosure is basic, acid addition salts of the compound of the compound can be made by reacting the free base of the compound with enough amount of desirable acid and adequate inert solvent. Pharmaceutically acceptable acid addition salt includes, but is not limited to, propionic acid, isobutylic acid, oxalic acid, malic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, hydrochloric acid, bromic acid, nitric acid, carbonic acid, monohydrogen-carbonic acid, phosphoric acid, monohydrogenphosphoric acid, dihydrogen-phosphoric acid, sulfuric acid, monohydrogen-sulfuric acid, hydrogen iodide, and phosphorous acid. In addition, the pharmaceutically acceptable salts of the present disclosure include, but are not limited to, a salt of amino acids such as arginate and an analog of organic acids such as glucuronic or galacturonic acids.

For example, a pharmaceutically acceptable salt of 2-hydroxy-5-[2-(4-trifluoromethyl phenyl)-ethylamino]-benzoic acid (Compound 2), a preferable example of the present disclosure, can be prepared using the method described in U.S. Pat. No. 8,598,383, which is herein incorporated by reference. However, the following reaction methods are offered by illustration and are not intended to limit the scope of the disclosure.

Some of the compounds of the present disclosure may be hydrated and exist in solvated or unsolvated forms. According to the present disclosure, some of the compounds exist in crystal or amorphous form, and any physical form is included in the scope of the present disclosure. Moreover, some compounds of the present disclosure may contain one or more asymmetric carbon atoms or double bonds. Therefore, they may exist in two or more stereoisomeric forms such as racemates, enantiomers, diastereomers, and geometric isomers, etc. The present disclosure includes these individual stereoisomers.

Compositions

The present disclosure also provides compositions comprising the 5-benzylaminosalicylic acid derivative represented by the above chemical formula (I) or its pharmaceutically acceptable salt and pharmaceutically acceptable excipient or additive for asthma, COPD, and ACOD. The 5-benzylaminosalicylic acid derivative represented by the above chemical formula (I) or its pharmaceutically acceptable salt of the present disclosure may be administered alone. In some embodiments, the composition comprising a compound of formula (I) is administered with a convenient carrier, diluent, etc.

In some embodiments, the composition dosage ranges from approximately 1 μg/kg to 200 mg/kg per day of the compound of formula (I). In some embodiments, the composition dosage ranges from approximately 10 μg/kg to 10 mg/kg per day of formula (I). However, the dosage may vary according to the patient condition or characteristics (age, sex, body weight, etc.), the severity of patients in need thereof, the effective components used, and the diets, etc. The compound of the present invention may be administered once a day or several times a day in divided doses, if necessary.

In some embodiments, the formulation may be administered as a single-dose or multiple-dose unit. In some embodiments, the composition comprises a single dose unit. In some embodiments, the composition comprises a multiple dose unit.

The composition for oral administration of the present disclosure may be formulated in solid or liquid form. Solid formulations include, but are not limited to, powders, granules, tablets, capsules, and suppositories. Moreover, the solid formulation may further include but is not limited to, a diluent, a flavoring agent, a binder, a preservative, a disintegrating agent, a lubricant, a filler, a plasticizer, etc. The liquid formulation includes, but is not limited to, a solution such as a water solution and propylene glycol solution, suspension, and emulsion, and may be prepared by adding suitable additives such as a coloring agent, flavoring agent, stabilizer, and thickener. In some embodiments, the composition is administered in a form selected from a capsule, a tablet, a powder, and a solution. In some embodiments, the composition is administered by mixing with a dietary supplement. In some embodiments, the composition is administered as a dietary supplement. In some embodiments, the composition is administered by mixing with food. In some embodiments, the composition is administered as a food composition. In some embodiments, the composition is administered by dissolving in water. In some embodiments, the composition is administered as a capsule with water. In some embodiments, the composition is administered as a chewable tablet.

For example, a powder can be prepared by mixing the 5-benzylaminosalicylic acid derivative of the present disclosure and pharmaceutically acceptable excipients, such as lactose, starch, and microcrystalline cellulose. A granule can be prepared by mixing the compound with a pharmaceutically acceptable excipient. In some embodiments, the pharmaceutically acceptable excipient comprises a diluent and/or a pharmaceutically acceptable binder. In some embodiments, the binders are polyvinylpyrrolidone, hydroxypropylcellulose, etc. In some embodiments, the composition is formed by wet granulation with adequate solvent(s) such as water, ethanol, and isopropanol, etc. In some embodiments, the composition is formed via direct compression with compression power. In addition, a tablet can be prepared by mixing the granule with a pharmaceutically acceptable lubricant, such as magnesium stearate, and tableting the mixture.

The pharmaceutical composition of the present disclosure may be administered in the form of, but not limited to, oral formulation, injectable formulation (for example, intramuscular, intraperitoneal, intravenous, infusion, subcutaneous, implant), inhalable, intranasal, vaginal, rectal, sublingual, transdermal, topical, etc., depending on the disorders to be treated and the animal's conditions. The composition of the present disclosure may be formulated in a suitable dosage unit comprising a pharmaceutically acceptable and non-toxic carrier, additive, and/or vehicle, which are all generally used in the art, depending on the route of administration. The depot type of formulation that can continuously release drugs for a desirable time is also included in the scope of the present disclosure.

EXPERIMENTAL EXAMPLES

The invention is now described with reference to the following examples: These examples are provided for the purpose of illustration only, and the invention should in no way be construed as being limited to these examples; rather, it should be construed to encompass any and all variations that become evident as a result of the teaching provided herein. The materials and methods used in these examples are as follows:

Material and Methods

Asthma

Seven-week-old female Balb/C mice were sensitized by intraperitoneal injection (IP, 200 μL/mouse) of 100 μg OVA complexed with aluminum potassium sulfate on days 0, 7, and 14. On days 26, 27, and 28, mice were challenged with 5% aerosolized OVA in 48 mL sterile phosphate-buffered saline (PBS). The control group received sterile PBS with aluminum potassium sulfate via the IP route on days 0, 7, 14, and 48 mL of aerosolized sterile PBS on days 26, 27, and 28. Mice in the ATPB group were orally administered 10 mg/kg bid ATPB on days 22, 27, 28, and 29.

COPD

As described previously, the rat model of COPD was established by smoke exposure and intratracheal instillation of lipopolysaccharide (LPS). Experimental rats, including the COPD and drug-treated groups (10 mg/kg ATPB), underwent whole-body exposure to tobacco smoke from 10 cigarettes in a tobacco smoke chamber (90×40×30 cm, made of Plexiglas) twice a day with 2-hour smoke-free intervals, every day for 12 weeks.

Animals from the two smoke-exposed groups were administered 180 μg/180 μL of LPS solution intratracheally on two occasions, on the first and 14th days of tobacco smoke exposure. Additionally, rats in the ATPB group were orally administered ATPB (10 mg/kg ATPB). All rats were sacrificed on the 91st day.

Porcine Pancreatic Elastase (PPE)-induced emphysema model was used to measure the post-treatment effects of ATPB in COPD model mice. C57BL/6J mice were intratracheally injected with PPE (0.8 U per mouse) in PBS via a micropipette. The mice were randomly divided into four groups: (A) emphysema group, which was exposed to intratracheal PPE; (B) emphysema+ATPB (5 mg/kg ATPB, PO, bid); (C) emphysema +ATPB (10 mg/kg ATPB, PO, bid); (D) emphysema +roflumilast (10 mg/kg, PO, qd); and (E) emphysema +prednisolone (1 mg/kg, PO, qd). All treatments were started 3 days after the PPE injection. Mice were sacrificed 21 days after the PPE injection.

Preparation of BALF and Cell Count

Rats and mice were sacrificed, and BALF was obtained by cannulating the trachea and lavage three times with 2 mL DPBS. BALF cells were centrifuged at 1000×g for 10 min at 4° C. The supernatants were collected and stored at −80° C. to measure inflammatory factors. The pelleted BALF cells were resuspended in 1 mL PBS and quantified using a hematology analyzer (Mindray Medical International Ltd., Shenzhen, China).

RNA Isolation and Real-Time PCR for Gene Expression

Total RNA from the lung tissue was extracted using TRIzol reagent (Invitrogen) according to the manufacturer's instructions. cDNA was synthesized using a cDNA Synthesis Kit (Life Technologies). SYBR Green Master Mix (Thermo Fisher) was used for PCR amplification on a StepOnePlus Real-Time PCR System (Applied Biosystems, Foster City, Calif., USA). Specific primers were designed, as shown in Table 1.

Histopathology

The lungs of the rats were removed at week 12 and fixed in 10% neutral buffered formalin for histopathological analysis. Formalin-fixed tissues were embedded in paraffin, sectioned at 3-5 mm, and stained with hematoxylin and eosin (HE) and Alcian blue-periodic acid-Schiff (AB-PAS) to reveal histopathological lesions.

Statistics Analysis

GraphPad Prism 5.0 was used for all statistical analyses. One-way analysis of variance (ANOVA) followed by Tukey's multiple comparisons test (for multiple groups) was used to analyze the differences between groups. All data were presented as means±standard errors of the means.

Results

Treatment with ATPB Attenuates the Production of IgE in the Serum

ELISA was performed to evaluate the effect of ATPB on IgE production. The results revealed that the production of IgE in the serum was higher in OVA-challenged mice than in normal control mice (FIG. 1). However, the increased level of IgE was significantly reduced in the ATPB-treated mice compared to that in the OVA-challenged mice.

Treatment with ATPB Decreases the Levels of Th2 Cytokines in the BALF

Figure 2:
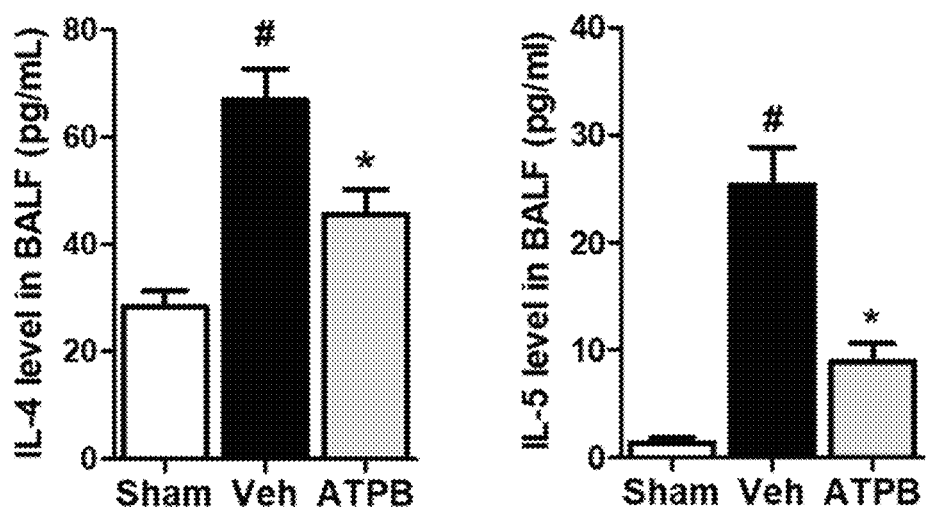
FIG. 2: Effects of ATPB on OVA-induced bronchoalveolar lavage fluid (BALF) cytokine levels are collected 24 h after the last OVA aerosol challenge. The levels of interleukin (IL)-4 and IL-5 were analyzed using ELISA.

As Th2 cytokines are involved in the airway inflammatory response in allergic asthma, the production of Th2 cytokines, including IL-4 and IL-5, was examined using ELISA. OVA-challenged mice exhibited a significant increase in IL-4 and IL-5 production compared to normal control mice. However, this level was significantly downregulated in the ATPB treatment group (FIG. 2).

Figure 3:
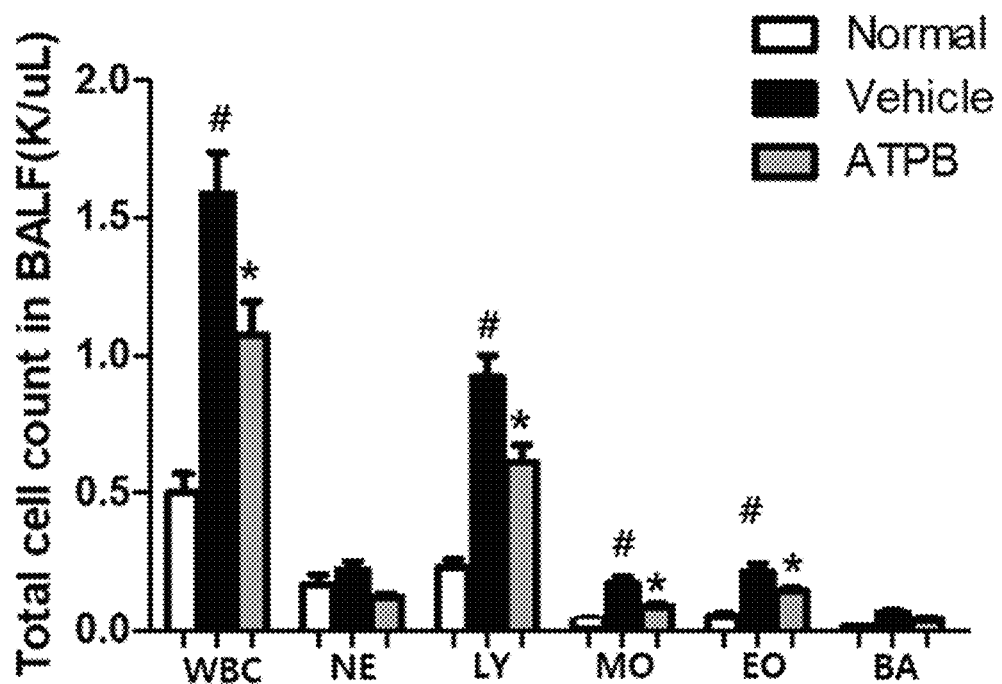
FIG. 3: Effects of ATPB on BALF cell infiltration. Inflammatory cell counts in BALF are obtained after the last saline aerosol or a 1-0 mg/mL OVA challenge. ATPB significantly reduced the OVA-induced inflammatory cell counts. The cell counts were performed on a minimum cell to identify eosinophils (EO), monocytes (MO), neutrophils (NE), and lymphocytes (LY).

Treatment with ATPB Attenuates the Inflammatory Cell in the BALF of Asthmatic Mice The OVA group had significantly elevated numbers of inflammatory cells, including WBCs, LY, MO, and EO, in the BALF ($p<0.05$) compared to the normal group (FIG. 3). The ATPB groups exhibited markedly reduced WBC, LY, MO, and EO cell counts, particularly eosinophils, compared with the vehicle group.

Figure 4:
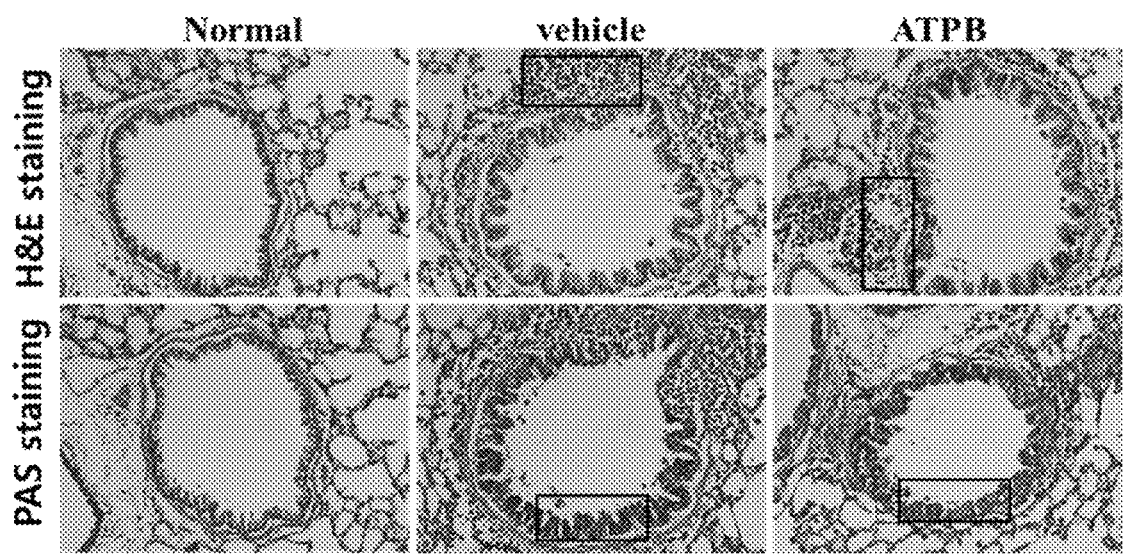
FIG. 4: Effects of ATPB on lung tissue eosinophilia and mucus production. Histological examination of lung tissue eosinophilia (upper panel, hematoxylin and eosin (H&E) staining, magnification) after the last challenge with saline OVA aerosol or OVA aerosol plus 10 mg/kg ATPB.

Treatment with ATPB Inhibits Inflammatory Cell Influx and Mucus Hypersecretion in the Lungs H&E staining was performed to determine whether ATPB affected inflammatory cell recruitment induced by OVA. In OVA-challenged mice, cell infiltration into peribranchial lung lesions was markedly increased. However, this cell infiltration was notably downregulated in the ATPB-treated mice. PAS staining was performed to assess the effects of ATPB on mucus production. The results revealed mucus hypersecretion in the bronchial airways of OVA-challenged mice. Notably, this level was attenuated in the lungs of mice in the ATPB treatment group compared to that in the lungs of OVA-challenged mice (FIG. 4). These results indicate that ATPB may be useful in airway inflammation via the suppression of inflammatory cell recruitment and mucus production (FIG. 4).

ATPB Decreases the Number of Inflammatory Cells in BALF

Figure 5:
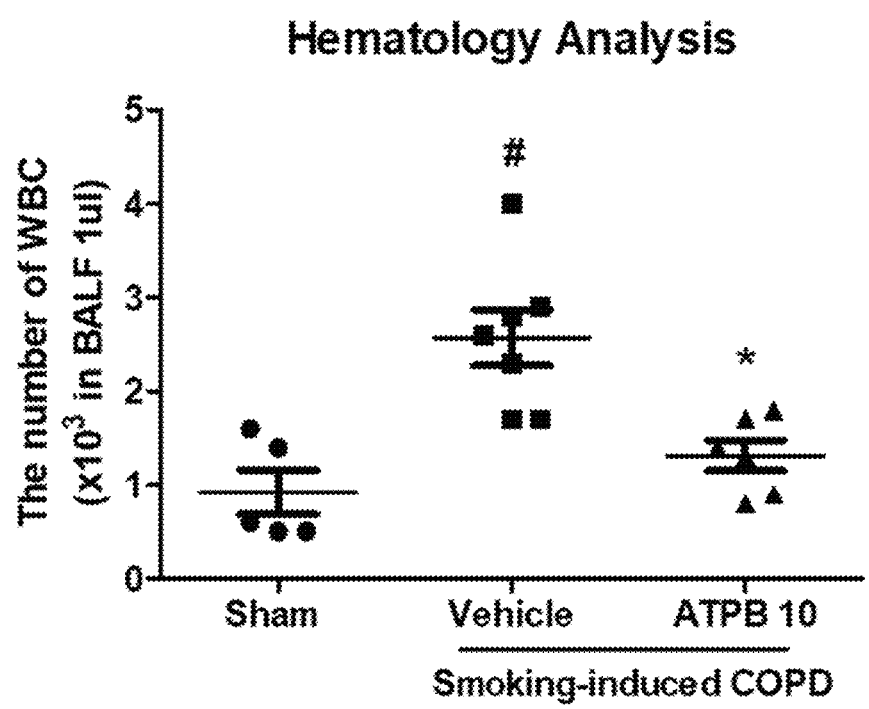
FIG. 5: Effects of ATPB on BALF cell infiltration.

To assess whether ATPB influenced inflammation in the lungs, the number of inflammatory cells in BALF was analyzed. As presented in FIG. 5, LPS and CS (chronic smoking) challenge resulted in increased numbers of total WBCs in BALF compared with the control group. Compared to that in the vehicle group, the ATPB group exhibited a markedly reduced number of WBCs.

ATPB Reduces Lung Inflammatory Response in Rat COPD Model

Figure 6:
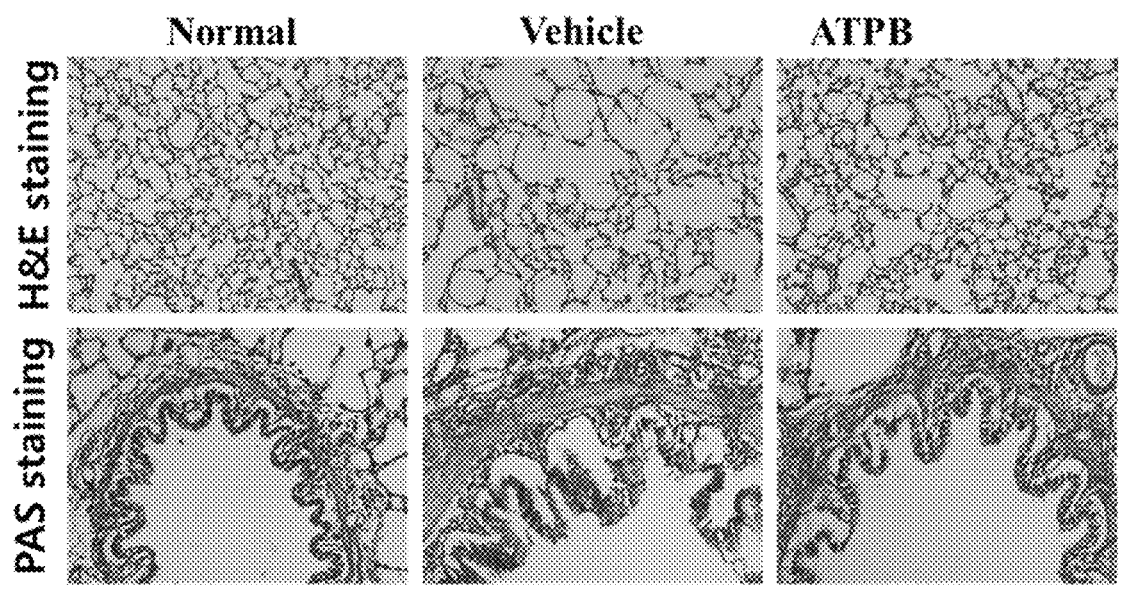
FIG. 6: Effects of ATPB on lung tissue eosinophilia and mucus production. Histological examination of lung tissue eosinophilia (upper panel, H&E staining, magnification ×400) and mucus secretion (right panel, PAS staining, magnification ×400) 3 months after smoking-induced COPD and smoking-induced COPD plus ATPB 10 mg/kg.

The effects of chronic smoking on the destruction of the alveolar structure were evaluated. Histopathological examination of hematoxylin and eosin-stained lung sections revealed bronchial mucosal epithelial cells necrosis in the chronic smoking group. The alveolar sacs and alveolar spaces were enlarged, and the alveolar walls were thickened (FIG. 6). After treatment with ATPB, the alveolar sacs and alveolar spaces were relieved compared with those in the COPD group (FIG. 6). ATPB protected against chronic smoking-induced pathological destruction and inflammatory infiltration in the lungs.

Goblet products in the tracheal epithelium were stained by PAS, and then a positive PAS-stained area was measured and analyzed as goblet metaplasia and mucus secretion. According to histological evaluation, goblet cell proliferation and mucus occlusion induced by cigarette smoke were significantly increased in the chronic smoking-induced rat model as compared to that of the ATPB group (FIG. 6). However, rats treated with ATPB (10 mg/kg) exhibited reduced levels of mucous secretion and decreased goblet cell proliferation (PAS+ cells) compared to that of the COPD rats (FIG. 6).

ATPB Treatment Reduces the mRNA of TNF-α, IL-1β, and MCP-1

Figure 7:
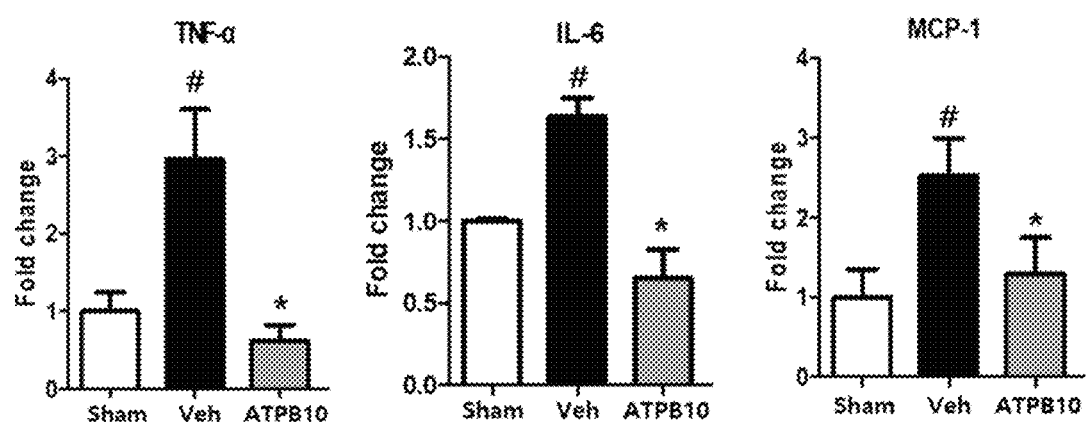
FIG. 7: Effects of ATPB on cytokine and chemokine levels in lung tissue. Lung tissue was collected three months after smoking. The IL-1β, TNFα, and Chemoattractant Protein-1 (MCP-1) levels were analyzed using quantitative polymerase chain reaction (PCR).

Gene expression of TNF-α, IL-6, and MCP-1 in the lungs was assessed using RT-PCR. In the COPD group, the mRNA expression levels of genes encoding TNF-α, IL-6, and MCP-1 were significantly higher than those in the control group (FIG. 7, $P<0.01$, or $P<0.05$). Compared with the COPD group, the gene expression levels of TNF-α, IL-6, and MCP-1 decreased in all ATPB treatment groups and the prednisolone group (FIG. 7, $P<0.01$, or $P<0.05$).

Post-Treatment ATPB Reduced Lung Inflammatory Response in Mouse COPD Model

Figure 8:
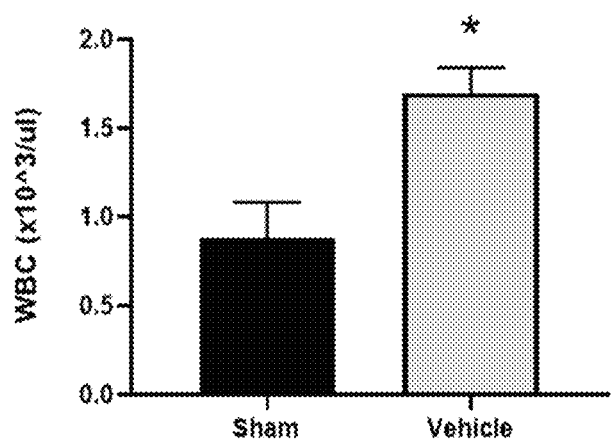
FIG. 8: Effects of ATPB post-treatment on BALF cell infiltration.
Figure 8:
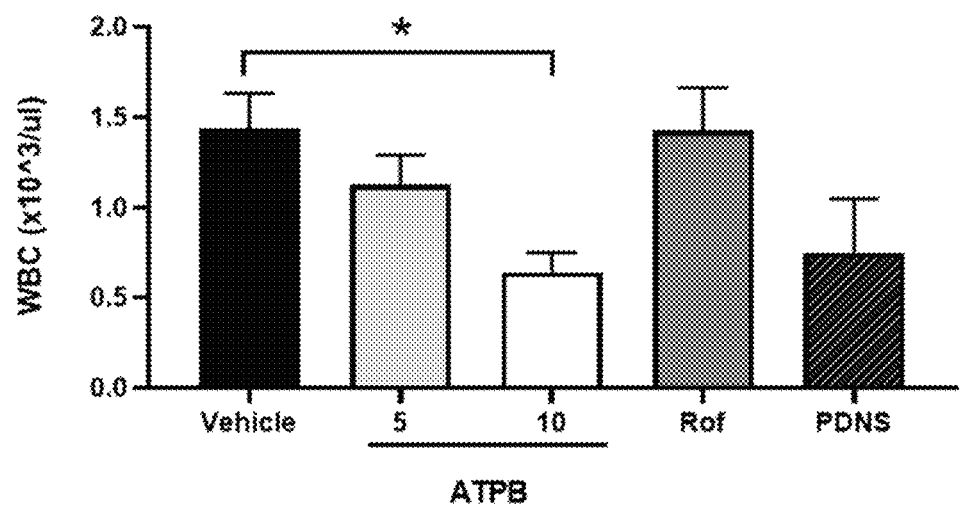

The number of WBCs in the BALF was measured to compare the effects of post-treatment with ATPB, roflumilast, or prednisolone after the induction of emphysema in PPE-induced COPD (FIG. 8, $P<0.05$). Each drug was administered from day d after PPE treatment, and the mice were sacrificed at 21 days. Compared to that in the vehicle group, the 10 mg/kg ATPB group exhibited a significantly reduced number of WBC. Neither roflumilast nor prednisolone reduced the WBC count.

INDUSTRIAL APPLICABILITY

The present study elucidates compounds comprising compound 18 (ATPB) and methods of administering a therapeutically effective amount of compound 18 for treating respiratory diseases such as asthma, COPD, and ACOD. The composition and methods of the present disclosure are useful for treating tissue impairment in pulmonary diseases.

Incorporation By Reference

All publications and patents mentioned herein are hereby incorporated by reference in their entirety as if each publication or patent was specifically and individually indicated to be incorporated by reference. In the case of a conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents and the specification, along with such variations.

REFERENCES

1. Lewis, B. W., et al., *Oxidative Stress Promotes Corticosteroid Insensitivity in Asthma and COPD*. Antioxidants (Basel), 2021. 10(9).
2. Crystal, R. G., *Airway basal cells. The "smoking gun" of chronic obstructive pulmonary disease*. Am J Respir Crit Care Med, 2014. 190(12): p. 1355-62.
3. Pauwels, R. A., et al., *Global strategy for the diagnosis, management, and prevention of chronic obstructive pulmonary disease: National Heart, Lung, and Blood Institute and World Health Organization Global Initiative for Chronic Obstructive Lung Disease (GOLD): executive summary*. Respir Care, 2001. 46(8): p. 798-825.
4. Walters, E. H., et al., *Fully integrating pathophysiological insights in COPD: an updated working disease model to broaden therapeutic vision*. Eur Respir Rev, 2021. 30(160).
5. Rabe, K. F., et al., *Effect of roflumilast in patients with severe COPD and a history of hospitalisation*. Eur Respir J, 2017. 50(1).
6. Barnes, P. J., *Inflammatory endotypes in COPD*. Allergy, 2019. 74(7): p. 1249-1256.
7. Fowdar, K., et al., *The effect of N-acetylcysteine on exacerbations of chronic obstructive pulmonary disease: A meta-analysis and systematic review*. Heart Lung, 2017. 46(2): p. 120-128.
8. Rogliani, P., et al., *Efficacy and safety profile of mucolytic/antioxidant agents in chronic obstructive pulmonary disease: a comparative analysis across erdosteine, carbocysteine, and N-acetylcysteine*. Respir Res, 2019. 20(1): p. 104.
9. Ryu, B. R., et al., *The novel neuroprotective action of sulfasalazine through blockade of NMDA receptors*. J Pharmacol Exp Ther, 2003. 305(1): p. 48-56.
10. Vane, J. R. and R. M. Botting, *The mechanism of action of aspirin*. Thromb Res, 2003. 110(5-6): p. 255-8.
11. Wu, K. K., *Aspirin and other cyclooxygenase inhibitors: new therapeutic insights*. Semin Vasc Med, 2003. 3(2): p. 107-12.
12. Lee, J. H., et al., *Prevention effects of ND-07, a novel drug candidate with a potent antioxidative action and anti-inflammatory action, in animal models of severe acute pancreatitis*. Eur J Pharmacol, 2012. 687(1-3): p. 28-38.
13. Hosseini, M., et al., *Global prevalence of asthma-COPD overlap (ACO) in the general population: a systematic review and meta-analysis*. Respir Res, 2019. 20(1): p. 229.

What is claimed:

1. A method of treating a pulmonary disease selected from asthma, COPD, ACOD, pulmonary fibrosis, pneumonia, and lung cancer, comprising:
administering to a subject in need thereof a therapeutically effective amount of a compound represented by the following formula or a pharmaceutically acceptable salt thereof:

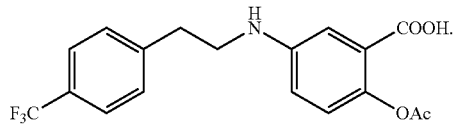 [SMILES: CC(=O)Oc1ccc(NCCc2ccc(C(F)(F)F)cc2)cc1C(=O)O]

2. The method of claim 1, wherein the pulmonary disease is selected from asthma, COPD, and ACOD.
3. The method of claim 1, further comprising conjointly administering one or more additional therapeutic agents for treating asthma to the subject.
4. The method of claim 3, wherein the one or more additional therapeutic agents for treating asthma are selected from corticosteroids; $\beta_2$ agonists; anticholinergics; leukotriene receptor antagonists or 5-lipoxygenase inhibitors; oral xanthines; anti-IgE antibody therapies; and anti-interleukin-5 therapies.
5. The method of claim 1, wherein the at least one pulmonary disease is COPD or ACOD.
6. The method of claim 5, further comprising conjointly administering one or more additional therapeutic agents for treating COPD or ACOD to the subject.
7. The method of claim 6, wherein the one or more additional therapeutic agents for treating COPD or ACOD are selected from corticosteroids; $\beta_2$ agonists with short-acting or long-acting bronchodilation; anticholinergics; long-acting muscarinic receptor antagonists (LAMAs); phosphodiesterase 4 (PDE4) inhibitors.
8. The method of claim 1, wherein the treating comprises reducing any pathologically increased TH2 cytokines in the subject.
9. The method of claim 1, wherein a dosage of about 1 µg/kg to about 200 mg/kg per day of the compound is administered to the subject.

* * * * *